United States Patent
Sato et al.

(10) Patent No.: US 6,242,449 B1
(45) Date of Patent: Jun. 5, 2001

(54) 3-BENZOYLINDOLE DERIVATIVES AND DRUGS CONTAINING THE SAME

(75) Inventors: Hiroki Sato; Mineo Takei; Jun Chikazawa; Yoichi Fukuda; Eiichi Nagano, all of Osato-gun (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/462,078

(22) PCT Filed: Jul. 15, 1998

(86) PCT No.: PCT/JP98/03169

§ 371 Date: Jan. 6, 2000

§ 102(e) Date: Jan. 6, 2000

(87) PCT Pub. No.: WO99/03831

PCT Pub. Date: Jan. 28, 1999

(30) Foreign Application Priority Data

Jul. 18, 1997 (JP) .................................................. 9-208301

(51) Int. Cl.⁷ ....................... A61K 31/496; C07D 403/12

(52) U.S. Cl. ...................................... 514/254.09; 544/373

(58) Field of Search ...................... 544/373; 514/254.09

(56) References Cited

FOREIGN PATENT DOCUMENTS

95/26955 * 12/1995 (WO) .

* cited by examiner

*Primary Examiner*—Emily Bernhardt
(74) *Attorney, Agent, or Firm*—Oblon, Spivak, McClelland, Maier & Neustadt, P.C.

(57) ABSTRACT

The present invention is directed to 3-benzoylindole derivatives represented by the following formula (I):

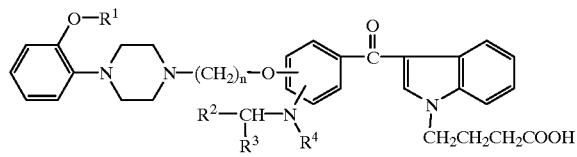

(wherein $R^1$ represents a lower alkyl group, n is an integer from 1 to 5; each of $R^2$ and $R^3$ represents a hydrogen atom, a lower alkyl group, or an optionally substituted phenyl group; and $R^4$ represents a hydrogen atom, a lower alkyl group, or a benzyl group) and to a pharmaceutical containing the same. This compound is endowed with strong $\alpha_1$-adrenergic receptor blocking action and strong testosterone 5α-reductase inhibitory action, as well as high level of safety, and thus is useful as an excellent preventive or therapeutic drug for prostatic hypertrophy or accompanying urination disorder, alopecia, and acne.

4 Claims, No Drawings

3-BENZOYLINDOLE DERIVATIVES AND DRUGS CONTAINING THE SAME

TECHNICAL FIELD

The present invention relates to novel 3-benzoylindole derivatives which have testosterone 5α-reductase inhibitory action and thus are effective in the treatment and/or prevention of diseases caused by overproduction of dihydrotestosterone, e.g., prostatic hypertrophy or accompanying urination disorder, male pattern alopecia, and acne (acne, pimples, etc.); and which have $\alpha_1$-adrenergic receptor blocking action and thus are capable of selectively curing disorders regarding passage through the bladder neck to thereby improve urination disorder.

BACKGROUND ART

Testosterone 5α-reductase is an enzyme that reduces testosterone, a male hormone (androgen), into dihydrotestosterone. The produced dihydrotestosterone has been elucidated to play an important role in the mechanism of the generation and progress of prostatic hypertrophy, male pattern alopecia, and acne (acne, pimples, etc.) (*J. Steroid Biochemistry*, 11, 609 (1979); *J. Clinical Endocrinol and Metabolism*, 56, 139 (1983); and Japanese Patent Application Laid-Open (kokai) No. 1-139558). Indoles are known as compounds that exhibit testosterone 5α-reductase inhibitory activities, (Japanese Patent Application Laid-Open (kokai) No. 4-244061, WO 93/02050).

α-Adrenergic receptors are known to participate in contraction of smooth muscles. Particularly, recent research has revealed that $\alpha_1$-adrenergic receptors strongly participate in contraction of the sphincter in the human bladder neck (J. Urol., 134, 396 (1985)). Therefore, blockers of the receptors are considered to serve as drugs that are capable of selectively treating urination disorders and frequent urination accompanied by prostatic hypertrophy. As compounds that have a blocking action against such $\alpha_1$-adrenergic receptors, there are known piperazine derivatives (WO89/12634, WO90/03972).

Disurea, which aged people frequently suffer, is caused by constriction of urethra due to the tonus of sympathetic nerves present in the bladder neck or by urinary obstruction associated with prostatic hypertrophy, and makes urination difficult. In recent years, disurea has been treated by the combined use of an $\alpha_1$-adrenergic receptor blocking agent and an anti androgenic agent. However, this is not satisfactory in view of the drug administration schedule.

Therefore, it is desired to develop drugs having both benefits of symptomatic therapy, which exerts immediate effects as exerted by $\alpha_1$-adrenergic receptors, and of radical therapy, which exhibits its effect slowly but radically, as in the case of testosterone 5a-reductase inhibitors.

Although International Patent Publication No. WO 95/26955 discloses indole derivatives that have both an $\alpha_1$-adrenergic receptor blocking action and a testosterone 5α-reductase inhibiting action in combination, further enhancement of the effects and activity thereof must be attained.

DISCLOSURE OF THE INVENTION

The present inventors have conducted earnest studies in order to solve the above-described problems, and have found that a certain group of 3-benzoylindole derivatives have both a strong α-adrenergic receptor blocking action and a strong testosterone 5α-reductase inhibiting action. The present invention has been accomplished on the basis of this finding.

Accordingly, the present invention provides a 3-benzoylindole derivative represented by following formula (I) or a salt thereof:

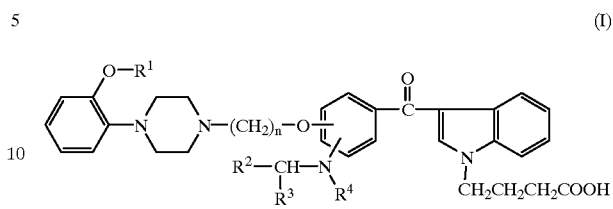

(I)

(wherein $R^1$ represents a lower alkyl group, n is an integer from 1 to 5; each of $R^2$ and $R^3$ are the same or different and each independently represents a hydrogen atom, a lower alkyl group, or a phenyl group which may have one or more substituents selected from among a lower alkyl group, a halo-substituted lower alkyl group, a lower alkoxy group, and a halogen atom; and $R^4$ represents a hydrogen atom, a lower alkyl group, or a benzyl group).

The present invention also provides a medicament comprising the above 3-benzoylindole derivative (I) or a salt thereof as an active ingredient.

The present invention also provides an $\alpha_1$-adrenergic receptor blocker and a testosterone 5α-reductase inhibitor comprising the above 3-benzoylindole derivative (I) or a salt thereof as an active ingredient.

The present invention also provides a preventive or therapeutic agent for prostatic hypertrophy, urination disorders associated with prostatic hypertrophy, alopecia, or acne, which comprises as an active ingredient the above 3-benzoylindole derivative (I) or a salt thereof.

The present invention also provides a pharmaceutical composition comprising the above 3-benzoylindole derivative (I) or a salt thereof and a pharmaceutically useful carrier.

The present invention also provides use of the above 3-benzoylindole derivative (I) or a salt thereof as a medicament.

The present invention also provides a method for treating prostatic hypertrophy, urination disorders associated with prostatic hypertrophy, alopecia, or acne, characterized by administering an effective amount of the above 3-benzoylindole derivative (I) or a salt thereof.

BEST MODE FOR CARRYING OUT THE INVENTION

In the present invention, unless specifically described otherwise, the term "lower" refers to a linear or branched carbon chain having 1 to 6 carbon atoms.

Accordingly, "lower alkyl groups" include, but are not limited to, methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1-ethylpropyl, 1,2-dimethylpropyl, hexyl, and isohexyl. Of these, linear or branched alkyl groups having 1 to 4 carbon atoms are preferred, with methyl, ethyl, propyl isopropyl, and butyl being particularly preferred.

Also "lower alkoxy groups" include, but are not limited to, methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1-ethylpropoxy, 1,2-dimethylpropoxy, hexyloxy, and isohexyloxy. Of these, linear or branched alkoxy groups having 1 to 4 carbon atoms are preferred, with methoxy and ethoxy being particularly preferred.

"Halogen atoms" include fluorine, chlorine, bromine, and iodine.

In the present invention, the term "halo-substituted lower alkyl group" refers to a group which is formed by bonding of one or more the above-described halogen atoms to one of the above-described lower alkyl group (represented as halo-substituted C1–C6 alkyl group). Specific examples include, but are not limited to, fluoromethyl, difluoromethyl, trifluoromethyl, chloromethyl, dichloromethyl, trichloromethyl, 2,2,2-trifluoroethyl, 2,2,2-trichloroethyl, 3,3,3-trifluoropropyl, 3,3,3-trichloropropyl, 4,4,4-trifluorobutyl, and 4,4,4-trichlorobutyl. These alkyl groups are preferably substituted by from 1 to 3 halogen atoms.

The term "phenyl group which may have one or more substituents selected from among a lower alkyl group, a halo-substituted lower alkyl group, a lower alkoxy group, and a halogen atom" refers to a phenyl group per se and a phenyl group of which benzene ring is substituted by one or more substituents selected from among a lower alkyl group, a halo-substituted lower alkyl group, a lower alkoxy group, and a halogen atom. Specific examples include phenyl, methylphenyl, ethylphenyl, propylphenyl, isopropylphenyl, butylphenyl, isobutylphenyl, methoxyphenyl, ethoxyphenyl, propoxyphenyl, isopropoxyphenyl, butoxyphenyl, isobutoxyphenyl, fluorophenyl, chlorophenyl, bromophenyl, (trifluoromethyl)phenyl, (chloromethyl)phenyl, (dichloromethyl)phenyl, (trichloromethyl)phenyl, (2,2,2-trifluoroethyl)phenyl, dimethylphenyl, diethylphenyl, dipropylphenyl, diisopropylphenyl, dibutylphenyl, diisobutylphenyl, dimethoxyphenyl, diethoxyphenyl, dipropoxyphenyl, diisopropoxyphenyl, dibutoxyphenyl, diisobutoxyphenyl, difluorophenyl, dichlorophenyl, dibromophenyl, di(trifluoromethyl)phenyl, di(chloromethyl)phenyl, di(dichloromethyl)phenyl, di(trichloromethyl)phenyl, di(2,2,2-trifluoroethyl)phenyl, trimethylphenyl, triethylphenyl, tripropylphenyl, truisopropylphenyl, tributylphenyl, triisobutylphenyl, trimethoxyphenyl, triethoxyphenyl, tripropoxyphenyl, triisopropoxyphenyl, tributoxyphenyl, triisobutoxyphenyl, trifluorophenyl, trichlorophenyl, tribromophenyl, methylfluorophenyl, methylchlorophenyl, and methylbromophenyl. The benzene ring of the phenyl groups preferably has 1 to 3 substituents.

Examples of preferred $R^2$ in formula (I) include hydrogen, lower alkyl, or phenyl. Examples of preferred $R^3$ include phenyl groups which may have one or more substituents selected from among a lower alkyl group, a halo-substituted lower alkyl group, a lower alkoxy group, and a halogen atom. The numeral "n" is preferably 2–4, with 3 being particularly preferred.

The compound (I) of the present invention forms salts with acids or bases. Examples of salts formed together with acids include mineral acids such as hydrochloric acid, hydrobromic acid, hydroiodic acid, sulfuric acid, nitric acid, and phosphoric acid; organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; and acidic amino acids such aspartic acid and glutamic acid. Examples of salts formed together with bases include inorganic bases such as sodium, potassium, magnesium, calcium, aluminum, and zinc; basic amino acids such as lysine and ornithine; and ammonium.

The present invention encompasses various solvates and crystalline polymorphisms of the compound (I) of the present invention, and moreover, optical isomers, racemic compounds, and R- and S-steroisomers of the compound (I) of the present invention.

The compound (I) of the present invention can be produced by a variety of synthesis methods, making use of characteristics on the basis of the backbone structure and kinds of substituents. Typical methods (methods A to C) will be described below. The compound of the present invention can be produced by any one of these methods or by any method that is accorded with these methods.

[Method A]

The compound of the present invention can be produced through steps (step A1 to step A4) described below:

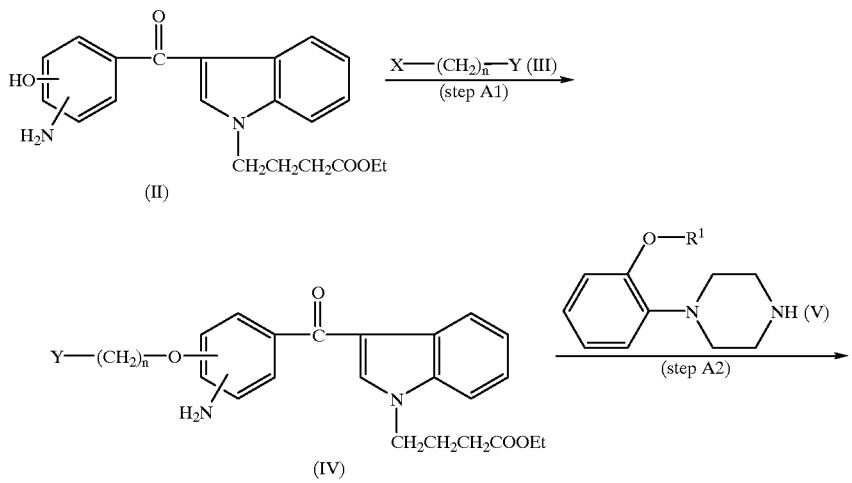

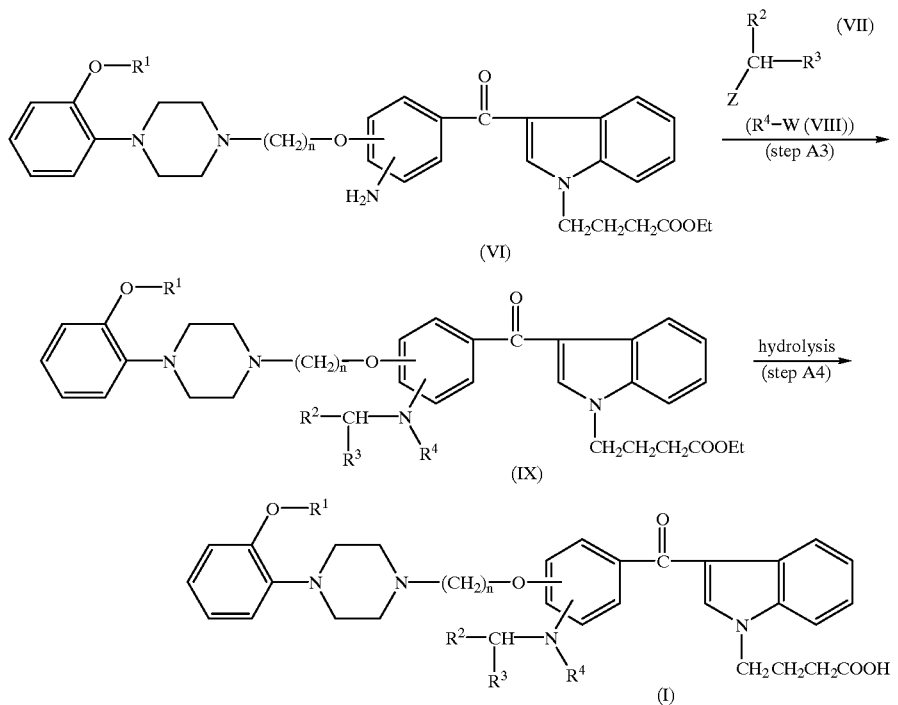

(wherein each of W, X, Y, and Z represents a halogen atom; and $R^1$, $R^2$, $R^3$, $R^4$, and n have the same meanings as mentioned above).

Step A1

Indole compound (II) disclosed in International Patent Publication WO 95/23143 with dihalogen compound (III), to thereby obtain halide compound (IV). The reaction is preferably performed in a solvent which does not affect the reaction, such as acetone, N,N-dimethylformamide, or methylene chloride, in the presence of a base, e.g., alkali metal carbonates such as potassium carbonate and sodium carbonate; trialkylamines such as triethylamine and diisopropylethylamine; and pyridines such as pyridine, lutidine, and 4-dimethylaminopyridine. The reaction temperature is not particularly limited, and the reaction may be performed with cooling or heating, at room temperature, or under warm conditions. Of two halogen atoms represented by X and Y in dihalogen compound (III), X preferably has a reactivity higher than that of Y.

Step A2

Halide (IV) is reacted with phenylpiperazine derivative (V), to thereby obtain compound (VI). The reaction may be performed under the same conditions as employed in step A1. When Y in halide (IV) is a chlorine atom, potassium iodide is preferably added for performing the reaction.

Step A3

Compound (VI) with alkyl halide (VII), to thereby obtain ester (IX). The reaction is performed in a manner similar to step A1.

When ester (IX) in which $R^4$ is other than a hydrogen atom is a target of production, a compound produced through reaction of compound (VI) and alkyl halide (VII) is further reacted with alkyl halide (VIII) in accordance with the procedure of step A1, to thereby obtain a target ester (IX).

Step A4

Ester (IX) is hydrolyzed to thereby obtain the compound (I) of the present invention. The reaction is typically performed in methanol, ethanol, tetrahydrofuran, or a mixed solvent containing water and the above organic solvent in the presence of a base, e.g., alkali metal hydroxides such as sodium hydroxide and potassium hydroxide and alkali metal carbonates such as sodium carbonate and potassium carbonate. The reaction may be performed at room temperature, under warm conditions, or with heating.

Furthermore, the compound (I) of the present invention is transformed into any of a variety of salts by a conventional method.

[Method B]

Compound (Ia) of the present invention—the compound (I) of the present invention in which $R^2$ is a hydrogen atom—can be produced by the following steps (step B1 to step B2) from compound (VI) prepared in accordance with Method A.

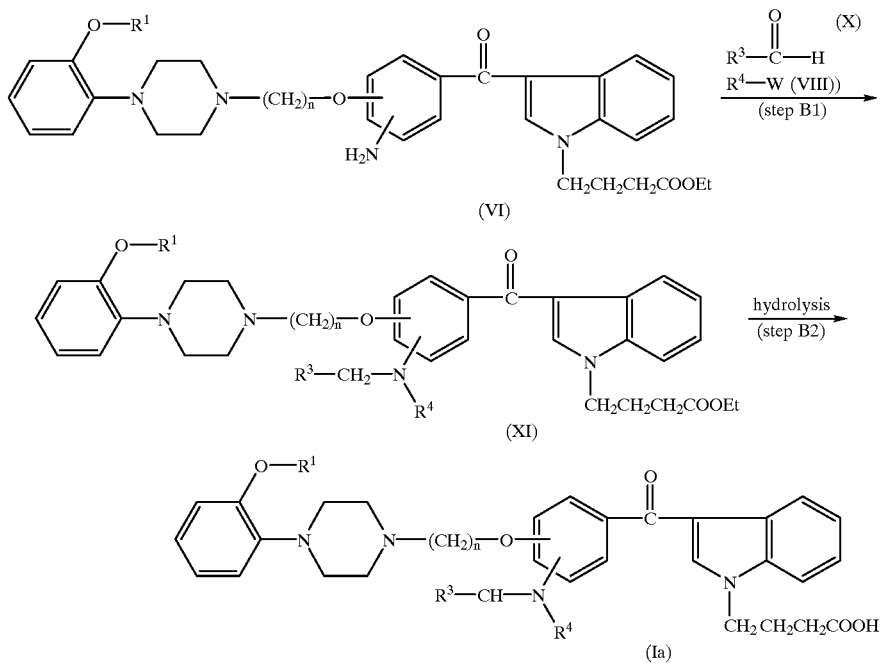

(wherein $R^1$, $R^3$, $R^4_1$ and n have the same definitions as mentioned above).

Step B1

Reductive alkylation of compound (VI), which is produced in step A2 of Method A, with aldehyde derivative (X) produces alkylaminobenzene derivative (XI). The reaction is typically performed in the presence of a reducing agent such as sodium borohydride or sodium cyanoborohydride, or in a hydrogen atmosphere in the presence of a catalyst such as palladium-carbon. Any solvent may be used so long as the solvent does not affect the reaction, and preferably used examples thereof include water, alcohol, acetic acid, and a mixture thereof. The reaction temperature is not particularly limited, and the reaction may be performed with cooling or heating, at room temperature, or under warm conditions.

When alkylaminobenzene derivative (XI) in which $R^4$ is other than a hydrogen atom is a target of production, a compound produced by reaction of compound (VI) and aldehyde derivative (X) is further reacted with alkyl halide (VIII) in accordance with the procedure of step A1, to thereby obtain a target alkylaminobenzene derivative (XI).

Step B2

Alkylaminobenzene derivative (XI) is hydrolyzed to thereby obtain compound (Ia) of the present invention; i.e., the compound (I) of the present invention in which $R^2$ is a hydrogen atom. The reaction is performed in a manner similar to step A4.

Furthermore, compound (Ia) is transformed into any of a variety of salts by a conventional method.

[Method C]

Compound (Ib) of the present invention—the compound (I) of the present invention in which $R^2$ and $R^4$ are both hydrogen atoms and $R^3$ is a phenyl group which may have a substituent—an be produced by steps (step C1 to step C4) described below:

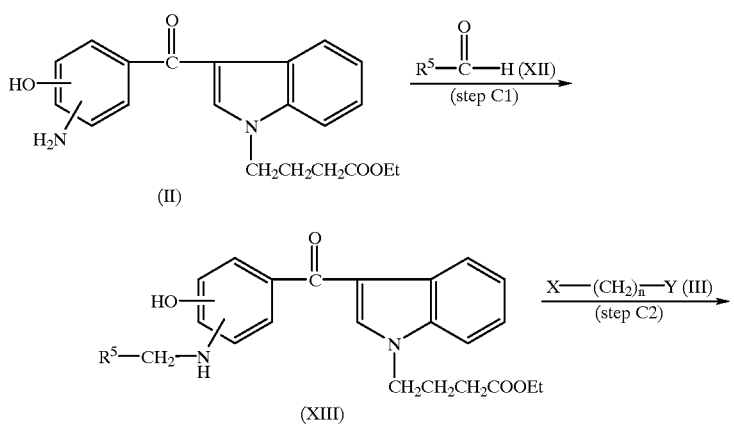

-continued

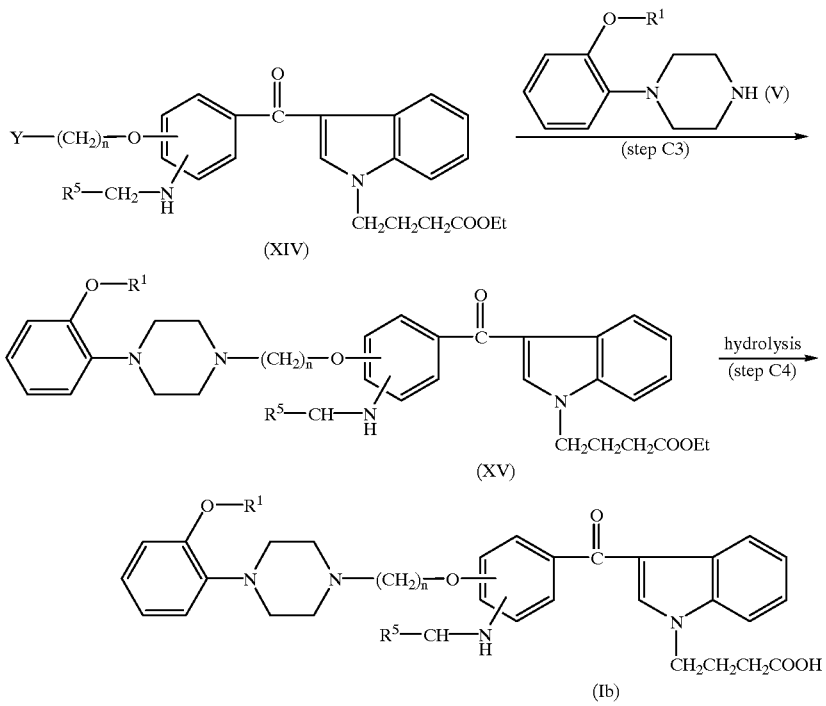

(wherein $R^5$ represents a phenyl group which may have a substituent; and $R^1$, X, Y, and n have the same meanings as mentioned above).

Step C1

Reductive alkylation of indole compound (II) which is disclosed in International Patent Publication WO 95/23143 with benzaldehyde derivative (XII) produces benzylphenylamine derivative (XIII). The reaction is performed in a manner similar to step B1.

Step C2

Benzylphenylamine derivative (XIII) is reacted with dihalogen compound (III), to thereby obtain halogen compound (XIV). The reaction is performed in a manner similar to Step A1.

Step C3

Halogen compound (XIV) is reacted with phenylpiperazine derivative (V), to thereby obtain ethyl butanoate compound (XV). The reaction is performed in a manner similar to step A2.

Step C4

Ethyl butanoate compound (XV) is hydrolyzed, to thereby obtain compound (Ib); i.e., the compound (I) of the present invention in which $R^2$ and $R^4$ are both a hydrogen atoms and $R^3$ is a phenyl group which may have a substituent. The reaction is performed in a manner similar to step A4.

Furthermore, compound (Ib) is transformed into any of a variety of salts by a conventional method.

As described below, the thus-obtained compound (I) of the present invention has an excellent $\alpha_1$-adrenergic receptor blocking action and an excellent testosterone 5α-reductase inhibitory action, as well as high safety. Thus, the compound is useful as a preventive or curing agent applied to disorders such as prostatic hypertrophy, disorders accompanying the same, such as urination disorder, male pattern alopecia, and acne (acne, pimples, etc.).

The compound (I) of the present invention, together with pharmaceutically accepted carriers and auxiliaries, my be formulated into preparations for oral administration. In order to prepare a medicament for oral administration, the compound is mixed with suitable additives, to thereby provide tablets, powders, granules, or capsules. Examples of additives include excipients such as lactose, mannitol, corn starch, and crystalline cellulose; binders such as cellulose derivatives, gum arabic, and gelatin; disintegrators such as calcium carboxymethylcellulose; and lubricants such as talc, and magnesium stearate. These solid medicaments may be formed into enteric medicaments by use of a coating base material such as hydroxypropylmethylcellulose phthalate, hydroxypropylmethylcellulose acetate succinate, cellulose acetate phthalate, or a methacrylate copolymer. In order to prepare a medicament for parenteral administration, the compound is combined with additives such as water, ethanol, glycerin, and a customary surfactants, to thereby provide injections, or is combined with a suppository base, to thereby provide suppositories.

The dosage may vary depending on age, body weight, and symptoms of the disease; curing effect; and the manner and period of administration. Generally, the compound is per-orally administered in a dose of 1–2000 mg/day, preferably 10–300 mg/day as divided in 1–3 times a day.

EXAMPLES

The present invention will next be described by way of examples, which should not be construed as limiting the invention thereto. Unless otherwise specified, MS data in Examples were obtained by fast atom bombardment mass spectrometry (FABMS).

Example 1 (Method C)
4-{3-{4-(4-Ethylphenyl)methylamino-3-{3-[4-(2-methoxyphenyl)piperazin-1-yl]propoxy}benzoyl}indol-1-yl}butanoic acid hydrochloride Step 1

Ethyl 4-[3-(4-amino-3-hydroxybenzoyl)indol-1-yl] butanoate (5.0 g) was suspended in a mixed solvent containing methanol (50 ml) and water (5 ml), and 4-ethylbenzaldehyde (3.66 g) and sodium cyanoborohydride (1.80 g) were added to the suspension. Acetic acid (2.5 ml) was further added dropwise to the mixture over five minutes, and the resultant mixture was stirred at room temperature for one hour. Water (50 ml) was added to the reaction mixture, and crystals so precipitated were collected by filtration. The produced crystals were recrystallized from ethanol, to thereby obtain 5.39 g of ethyl 4-{3-[4-( 4-ethylphenyl) methylamino-3-hydroxybenzoyl)indol-1-yl}butanoate as yellow crystals.

Melting point: 133–134° C. (decomposed); MS(m/z): 485(MH$^+$); IR(KBr)cm$^{-1}$: 3400, 1709, 1601; NMR(CDCl$_3$) δ: 1.15~1.30(m, 6H), 2.17(quint, 2H), 2.29(t, 2H), 2.64(q, 2H), 4.09(q, 2H), 4.20(t, 2H), 4.40(s, 2H), 4.90~5.30(br, 1H), 6.53(d, 1H), 7.18(d, 2H), 7.24~7.44(m, 6H), 7.62(s, 1H), 7.86(d, 1H), 8.30~8.60(m, 2H).

Step 2

Ethyl 4-{3-[4-(4-ethylphenyl)methylamino-3-hydroxybenzoyl]indol-1-yl}butanoate (39.3 g) was dissolved in N,N-dimethylformamide (200 ml), and potassium carbonate (22.4 g) and chlorobromopropane (24 ml) were added to the solution. The mixture was stirred at room temperature for four hours. The reaction mixture was poured into water, and ethyl acetate was further added for extraction. The formed organic layer was sequentially washed with 1N hydrochloric acid, saturated sodium bicarbonate, and brine, and dried. The solvent was evaporated under reduced pressure. The residue was purified by silica gel column chromatography (n-hexane:ethyl acetate=3:1), to thereby obtain 44.8 g of ethyl 4-{3-[3-chloropropoxy-4-(4-ethylphenyl)methylaminobenzoyl]indol-1-yl}butanoate as a yellow oil. MS(m/z): 562(MH$^+$); IR(CHCl$_3$)cm$^{-1}$:3450, 1730, 1595; NMR(CDCl$_3$)δ:1.21(t, 3H), 1.25(t, 3H), 2.13~2.36(m, 6H), 2.66(q, 2H), 3.72(t, 2H), 4.10(q, 2H), 4.21~4.31(m, 4H), 4.43(d, 2H), 5.03(t, 1H), 6.59(d, 1H), 7.08~7.50(m, 9H), 7.60(s, 1H), 8.31~8.37(m, 1H).

Step 3

Ethyl 4-{3-[3-chloropropoxy-4-(4-ethylphenyl) methylaminobenzoyl]indol-1-yl}butanoate (44.5 g) was dissolved in N,N-dimethylformamide (230 ml), and 1-(2-methoxyphenyl)piperazine hydrochloride (36.2 g), potassium iodide (52.5 g), and triethylamine (46 ml) were added to the solution. The resultant mixture was stirred at 90° C. for one hour. The reaction mixture was cooled and poured into ethyl acetate (230 ml) and 1N hydrochloric acid (460 ml) was added. Crystals so precipitated were collected by filtration and recrystallized from 90% ethanol, to thereby obtain 42.6 g of ethyl 4-{3-{4-(4-ethylphenyl)methylamino-3-{3-[4-(2-methoxyphenyl)piperazin-1-yl]propoxy}benzoyl}indol-1-yl}butanoate hydrochloride as colorless crystals.

Melting point: 178–179° C.; MS(m/z): 717(MH$^+$—HCl); IR(KBr)cm$^{-1}$: 3308, 1732, 1590; NMR(CDCl$_3$)δ: 1.15~1.30 (m, 6H), 2.19(quint, 2H), 2.31(t, 2H), 2.45~2.70(m, 4H), 2.90~3.35(m, 4H), 3.40~3.70(m, 6H), 3.86(s, 3H), 4.08(q, 2H), 4.15~4.30(m, 4H), 4.47(brs, 2H), 5.67(brs, 1H), 6.55(d, 1H), 6.80~7.50(m, 13H), 7.61 (s, 1H), 8.25~8.30(m, 1H), 12.77(brs, 1H)

Step 4

Ethyl 4-{3-{4-(4-ethylphenyl)methylamino-3-{3-[4-(2-methoxyphenyl)piperazin-1-yl]propoxy}benzoyl}indol-1-yl}butanoate hydrochloride (40.8 g) was dissolved in tetrahydrofuran (200 ml), and methanol (200 ml) and potassium hydroxide (11.3 g) were added to the solution. The resultant mixture was refluxed for one hour and 30 minutes. The reaction mixture was cooled and concentrated under reduced pressure. Water (1.2 l) was added to dilute the residue, and the resultant solution was poured into 1N hydrochloric acid (400 ml), to thereby precipitate crystals. The crystals were collected by filtration. The collected crystals were washed with water, dried, and recrystallized from 95% ethanol, to thereby obtain 33.8 g of 4-{3-{4-(4-ethylphenyl)methylamino-3-{3-[4-(2-methoxyphenyl) piperazin-1-yl]propoxy}benzoyl}indol-1-yl}butanoate hydrochloride as pale yellow crystals.

Melting point: 152–155° C.; MS(m/z): 689(MH$^+$—HCl); IR(KBr)cm$^{-1}$: 3297, 1710, 1589; NMR(DMSO-d$_6$)δ: 1.16(t, 3H), 2.03(quint, 2H), 2.18~2.42(m, 4H), 2.56(q, 2H), 2.90~3.70(m, 13H), 4.20~4.40(m, 4H), 4.47(d, 2H), 6.44~6.65(m, 2H), 6.85~7.08(m, 4H), 7.12~7.42(m, 8H), 7.60(d, 1H), 8.03(s, 1H), 8.18~8.26(m, 1H), 11.00~12.50(br, 2H).

Example 2 (Method A)

4-{3-{4-Diphenylmethylamino-3-{3-[4-(2-methoxyphenyl) piperazin-1-yl]propoxy}benzoyl}indol-1-yl}butanoic acid hydrochloride Step 1

Ethyl 4-[3-(4-amino-3-hydroxybenzoyl)indol-1-yl] butanoate (30 g) was suspended in acetone (390 ml), potassium carbonate (23.8 g) and chlorobromopropane (24 ml) were added to the suspension. The mixture was stirred at room temperature for four hours. The reaction mixture was cooled and filtrated. The filtrate was concentrated under reduced pressure. The resultant residue was purified by silica gel column chromatography (n-hexane:ethyl acetate=2:1), to thereby obtain 22.8 g of ethyl 4-{3-[4-amino-3-(3-chloropropoxy)benzoyl]indol-1-yl}butanoate as colorless prisms.

Melting point: 93–95° C.; MS(m/z): 443(MH$^+$); IR(KBr) cm$^{-1}$: 3450, 3322, 1725, 1624; NMR(CDCl$_3$)δ: 1.22(t, 3H), 2.15~2.40(m, 6H), 3.75(t, 2H), 4.10(q, 2H), 4.19(s, 2H), 4.20~4.30(m, 4H), 6.72(d, 1H), 7.25~7.48(m, 5H), 7.61(s, 1H), 8.30~8.39(m, 1H).

Step 2

Ethyl 4-{3-[4-amino-3-(3-chloropropoxy)benzoyl]indol-1-yl}butanoate (22.8 g) was dissolved in N,N-dimethylformamide (115 ml), and 1-(2-methoxyphenyl) piperazine hydrochloride (12.9 g), potassium iodide (17.1 g), potassium carbonate (17.8 g) were added to the solution. The thus-produced mixture was stirred at 90° C. for one hour. The reaction mixture was cooled and diluted with ethyl acetate (200 ml). The formed solution was sequentially washed with water and saturated brine, and dried. The solution was concentrated under reduced pressure. A'4N solution (28 ml) of hydrochloric acid in dioxane was added to the residue, and crystals so precipitated were collected by filtration. The collected crystals were recrystallized from ethanol, to thereby obtain 27.4 g of ethyl 4-{3-{4-amino-3-{3-[4-(2-methoxyphenyl)piperazin-1-yl] propoxy}benzoyl}indol-1-yl}butanoate hydrochloride as yellow crystals.

Melting point: 130–135° C. (decomposed); MS(m/z): 599(MH$^+$—HCl); IR(KBr)cm$^{-1}$: 3432, 1726, 1620; NMR (DMSO-d$_6$)δ: 1.09(t, 3H), 1.99~2.15(m, 2H), 2.22~2.40(m, 4H), 3.06~3.34(m, 4H), 3.42~3.73(m, 6H), 3.81(s, 3H), 3.96(q, 2H), 4.20~4.44(m, 4H), 6.87~7.10(m, 4H), 7.22~7.39(m, 3H), 7.39~7.49(m, 2), 7.65(d, 1H), 8.11(s, 1H), 8.26(d, 1H), 11.20(brs, 1H).

Step 3

Ethyl 4-{3-{4-amino-3-{3-[4-(2-methoxyphenyl) piperazin- 1-yl]propoxy}benzoyl}indol-1-yl}butanoate hydrochloride (2.0 g) was dissolved in N,N-dimethylformamide (10 ml), and diphenylmethyl chloride (1.2 ml) and potassium carbonate (1.3 g) were added to the solution. The mixture was stirred at 90° C. for five hours. The reaction mixture was cooled and diluted with ethyl acetate (200 ml). The resultant mixture was sequentially washed with water and saturated brine, and dried and evaporated under reduced pressure. The resultant residue was purified by silica gel column chromatography (n-hexane:ethyl acetate=1:1), to thereby obtain 1.13 g of ethyl 4-{3-{4-diphenylmethylamino-3-{3-[4-(2-methoxyphenyl)piperazin-1-yl]propoxy}benzoyl}indol-1-yl}butanoate as a pale yellow oil.

MS(m/z): 765(MH$^+$); IR(KBr)cm$^{-1}$: 3400, 1730, 1595; NMR(CDCl$_3$)δ: 1.19(t, 3H), 1.97~2.33(m, 6H), 2.50~2.67 (m, 6H), 3.00~3.12(m, 4H), 3.87(s, 3H), 4.08(q, 2H), 4.17~4.27(m, 4H), 5.27(d, 1H), 5.61(d, 1H), 6.40(d, 1H), 6.83~7.03(m, 4H), 7.24~7.42(m, 14H), 7.46(d, 1H), 7.56(s, 1H), 8.31~8.38(m, 1H).

Step 4

The procedure of step 4 of Example 1 was repeated except that ethyl 4-{3-{4-diphenylmethylamino-3-{3-[4-(2-methoxyphenyl)piperazin-1-yl]propoxy}benzoyl}indol-1-yl}butanoate was used instead of ethyl 4-{3-{4-(4-ethylphenyl)methylamino-3-{3-[4-(2-methoxyphenyl)piperazin-1-yl]propoxy}benzoyl}indol-1-yl}butanoate hydrochloride, to thereby yield 4-{3-{4-diphenylmethylamino-3-{3-[4-(2-methoxyphenyl)piperazin-1-yl]propoxy}benzoyl}indol-1-yl}butanoic acid hydrochloride.

MS(m/z): 737(MH$^+$—HCl); IR(KBr)cm$^{-1}$: 3410, 1723, 1595; NMR(DMSO-d$_6$)δ: 1.95~2.09(m, 2H), 2.18~2.31(m, 4H), 2.90~3.70(m, 11H), 3.80(s, 3H), 4.20~4.34(m, 4H), 5.67(d, 1H), 5.85(d, 1H), 6.59(d, 1H), 6.89~7.06(m, 4H), 7.19~7.52(m, 14H), 7.61(d, 1H), 8.02(s, 1H), 8.21 (d 1H), 10.00~11.00(br, 1H).

Example 3 (Method B)

4-{3-{3-{3-[4-(2-Methoxyphenyl)piperazin-1-yl]propoxy}-4-[(4-trifluoromethylphenyl)methylamino]benzoyl}indol-1-yl}butanoic acid hydrochloride Step 1

Ethyl 4-{3-{4-amino-3-{3-[4-(2-methoxyphenyl)piperazin-1-yl]propoxy}benzoyl}indol-1-yl}butanoate hydrochloride (2.0 g) was suspended in a mixed solvent containing methanol (18 ml) and water (2 ml), and 4-trifluoromethylbenzaldehyde (1.64 g) and sodium cyanoborohydride (0.62 g) were added to the suspension. The resultant mixture was stirred overnight at room temperature. Water was added to the reaction mixture, and the mixture was extracted with chloroform. The organic layer was sequentially washed with water, saturated sodium bicarbonate, and brine, dried and evaporated under reduced pressure. The resultant residue was purified by silica gel column chromatography (n-hexane:ethyl acetate=1:5), and 1N hydrochloric acid was added to the purified residue. The mixture was extracted with chloroform. The chloroform layer was washed with brine, dried, and evaporated under reduced pressure. Ethanol was added to the resultant residue for crystallization. Thus, 1.53 g of ethyl 4-{3-{3-{3-[4-(2-methoxyphenyl)piperazin-1-yl]propoxy}-4-[(4-trifluoromethylphenyl)methylamino]benzoyl}indol-1-yl}butanonate hydrochloride as white crystals.

Melting point: 215–218° C. (decomposed); MS(m/z): 757(MH$^+$—HCl); IR(KBr)cm$^{-1}$: 3287, 1736, 1593; NMR (CDCl$_3$)δ: 1.18(t, 3H), 2.19(q, 2H), 2.30(t, 2H), 2.45~2.63 (m, 2H), 3.00~3.22(m, 2H), 3.25~3.40(m, 2H), 3.45~3.57 (m, 4H), 3.60~3.63(m, 2H), 3.86(s, 3H), 4.07(q, 2H), 4.15~4.30(m, 4H), 4.60(s, 2H), 6.35(brs, 1H), 6.38(d, 1H), 6.85~6.98(m, 3H), 7.00~7.12(m, 1H), 7.20~7.46(m, 5H), 7.47~7.65(m, 5H), 8.28~8.37(m, 1H), 12.57(brs, 1H).

Step 2

The procedure of step 4 of Example 1 was repeated except that ethyl 4-{3-{3-{3-[4-(2-methoxyphenyl)piperazin-1-yl]propoxy}-4-[(4-trifluoromethylphenyl)methylamino]benzoyl}indol-1-yl}butanoate hydrochloride was used instead of ethyl 4-{3-{4-(4-ethylphenyl)methylamino-3-{3-[4-(2-methoxyphenyl)piperazin-1-yl]propoxy}benzoyl}indol-1-yl}butanoate hydrochloride, to thereby obtain 4-{3-{3-{3-[4-(2-methoxyphenyl)piperazin-1-yl]propoxy}-4-[(4-trifluoromethylphenyl)methylamino]benzoyl}indol-1-yl}butanoic acid hydrochloride.

Melting point: 145–148° C. (decomposed); MS(m/z): 729(MH$^+$—HCl); IR(KBr)cm$^{-1}$: 3291, 1717, 1592; NMR (DMSO-d$_6$)δ: 1.95~2.10(m, 2H), 2.24(t, 2H), 2.35(brs, 2H), 3.03~3.72(m, 10H), 3.80(s, 3H), 4.18~4.27(m, 2H), 4.30(t, 2H), 4.62(brs, 2H), 6.44(d, 1H), 6.71(brs, 1H), 6.85~7.07(m, 4H), 7.18~7.40(m, 4H), 7.56~7.67(m, 3H), 7.72(d, 2H), 8.02(s, 1H), 8.21 (d, 1H), 10.90(brs, 1H), 12.15(brs, 1H).

Examples 4 to 26

The procedure of any one of Examples 1 to 3 was carried out with choice of appropriate starting compounds, to thereby obtain compounds of Example 4 to 26.

Example 4

4-{3-{4-(4-Ethylphenyl)methylamino-3-{3-[4-(2-methoxyphenyl)piperazin-1-yl]propoxy}benzoyl}indol-1-yl}butanoic acid Melting point: 137–138° C.; MS(m/z) : 689(MH$^+$); IR(KBr)cm$^{-1}$: 3422, 1592; NMR(DMSO-d$_6$)δ: 1.16(t, 3H), 1.93~2.15(m, 4H), 2.17~2.27(m, 2H), 2.57(q, 2H), 2.60~3.20(m, 10H), 3.77(s, 3H), 4.17(t, 2H), 4.29(t, 2H), 4.43(d, 2H), 6.30(t, 1H), 6.49(d 1H), 6.79~7.01(m, 4H), 7.10~7.40(m, 9H), 7.59(d, 1H), 7.99(s, 1H), 8.19(d, 1H).

Example 5

Potassium 4-{3-{3-{3-[4-(2-methoxyphenyl)piperazin-1-yl]propoxy}-4-benzylamino}benzoyl}indol-1-yl}butanoate MS(m/z): 699(MH$^+$); IR(KBr)cm$^{-1}$: 1593, 1571; NMR (CD$_3$OD)δ: 2.03~2.26(m, 6H), 2.51~2.72(m, 6H), 3.00~3.09(m, 4H), 3.84(s, 3H), 4.23(t, 2H), 4.29(t, 2H), 4.49(s, 2H), 6.64(d, 1H), 6.83~7.02(m, 4H), 7.17~7.46(m, 9H), 7.55(d, 1H), 7.86(s, 1H), 8.19(d, 1H).

Example 6

Potassium 4-{3-{3-{3-[4-(2-methoxyphenyl)piperazin-1-yl]propoxy}-4-dibenzylamino}benzoyl}indol-1-yl}butanoate MS(m/z): 789(MH$^+$); IR(KBr)cm$^{-1}$: 1588, 1569; NMR (CD$_3$OD)δ: 1.98~2.23(m, 6H), 2.50~2.67(m, 6H), 3.01(brs, 4H), 3.84(s, 3H), 4.24(t, 2H), 4.29(t, 2H), 4.44(s, 4H), 6.83~7.03(m, 5H), 7.16~7.43(m, 14H), 7.47(d, 1H), 7.58(d, 1H), 7.92(s. 1H), 8.24(d, 1H).

Example 7

Potassium 4-{3-{3-{3-[4-(2-methoxyphenyl)piperazin-1-yl]propoxy}-4-(4-methylphenyl)methylamino}benzoyl}indol-1-yl}butanoate MS(m/z): 713(MH$^+$); IR(KBr)cm$^{-1}$: 1593, 1571; NMR (DMSO-d$_6$)δ: 1.84~2.08(m, 6H), 2.26(s, 3H), 2.45~2.64(m, 6H), 2.94(brs, 6H), 3.76(s, 3H), 4.15(t, 2H), 4.25(t, 2H), 4.41(d, 2H), 6.20(t, 1H), 6.48(d, 1H), 6.78~6.98(m, 4H), 7.08~7.38(m, 8H), 7.61(d, 1H), 7.95(s, 1H), 8.18(d, 1H).

Example 8
4-{3-{4-[(4-Methylphenyl)methylamino]-3-{3-[4-(2-ethoxyphenyl)piperazin-1-yl]propoxy}benzoyl}indol-1-yl}butanoic acid Melting point: 128–130° C.; MS(m/z): 689(MH$^+$); IR(KBr)cm$^{-1}$: 3389, 1595; NMR(DMSO-d$_6$)δ: 1.33(t, 3H), 1.97~2.07(m, 6H), 2.25(s, 3H), 2.49~2.55(m, 6H), 2.96(brs, 4H), 3.79(q, 2H), 4.14~4.25(m, 4H), 4.40(s, 2H), 6.23(br, 1H), 6.48(d, 1H), 6.80~6.87(m, 4H), 7.10~7.36(m, 8H), 7.60(d, 1H), 7.96(s, 1H), 8.20(d, 1H).

Example 9
4-{3-{4-[N-(4-Methylphenyl)methyl-N-methylamino]-3-{3-[4-(2-methoxyphenyl)piperazin-1-yl]propoxy}benzoyl}indol-1-yl}butanoic acid MS(m/z): 689(MH$^+$); IR(KBr)cm$^{-1}$: 1508, 1242; NMR(DMSO-d$_6$)δ: 1.89~2.00(m, 6H), 2.28(s, 3H), 2.39~2.41(m, 6H), 2.70(s, 3H), 2.89(br, 4H), 3.76(s, 3H), 4.11~4.30(m, 4$_1$H), 4.35(s, 2H), 6.80~6.95(m, 5H), 7.12~7.66(m, 9H), 8.04(s, 1H), 8.22~8.25(m, 1H).

Example 10
4-{3-{3-{3-[4-(2-Ethoxyphenyl)piperazin-1-yl]propoxy}-4-[(4-ethylphenyl)methylamino]benzoyl}indol-1-yl}butanoic acid Melting point: 134–137° C.; MS(m/z): 703(MH$^+$); IR(KBr)cm :3368, 1595, 1572; NMR(DMSO-d$_6$)δ: 1.16(t, 3H), 1.35(t, 3H), 1.98~2.25(m, 6H), 2.57(q, 2H), 2.60~3.80 (br, 10H), 4.02(q, 2H), 4.18(br, 2H), 4.29(br, 2H), 4.43(d, 2H), 6.35(br, 1H), 6.49(d, 1H), 6.82~6.96(m, 4H), 7.13~7.37(m, 8H), 7.59(d, 1H), 7.99(s, 1H), 8.19(d, 1H).

Example 11
4-{3-{4-[(4-Ethylphenyl)methylamino]-3-{2-[4-(2-methoxyphenyl)piperazin-1-yl]ethoxy}benzoyl}indol-1-yl}butanoic acid hydrochloride MS(m/z): 675(MH$^+$—HCl); IR(KBr)cm$^{-1}$: 3430, 1720, 1593; NMR(DMSO-d$_6$)δ: 1.14(t, 3H), 2.02(quint, 2H), 2.24(t, 2H), 2.56(q, 2H), 3.00~3.90(m, 15H), 4.30(t, 2H), 4.38~4.50(m, 4H), 6.50(d, 1H), 6.87~7.05(m, 4H), 7.12~7.43(m, 8H), 7.60(d, 1H), 8.02(s, 1H), 8.21(dd, 1H), 10.80~12.00(br, 1H).

Example 12
4-{3-{4-[(4-Ethylphenyl)methylamino]-3-{4-[4-(2-methoxyphenyl)piperazin-1-yl]butoxy}benzoyl}indol-1-yl}butanoic acid hydrochloride MS(m/z): 703(MH$^+$—HCl); IR(KBr)cm$^{-1}$: 3410, 1720, 1593; NMR(DMSO-d$_6$)δ: 1.15(t, 3H), 1.81~2.08(m, 6H), 2.23(t, 2H), 2.56(q, 2H), 2.80~4.00(m, 14H), 4.10~4.19(m, 2H), 4.29(t, 2H), 4.44(d, 2H), 6.29(t, 1H), 6.50(d, 1H), 6.85~7.04(m, 4H), 7.13~7.39(m, 8H), 7.60(d, 1H), 7.99(s, 1H), 8.20(dd, 1H).

Example 13
4-{3-{4-[(4-Ethylphenyl)methylamino]-3-{3-[4-(2-propoxyphenyl)piperazin-1-yl]propoxy}benzoyl}indol-1-yl}butanoic acid dihydrochloride Melting point: 170–183° C. (decomposed); MS(m/z): 717(MH$^+$—2HCl); IR(KBr)cm$^{-1}$: 3306, 1707, 1592; NMR(DMSO-d$_6$)δ: 1.02(t, 3H), 1.16(t, 3H), 1.77(sext, 2H), 2.01(quint, 2H), 2.17~2.30(m, 4H), 2.57(q, 2H), 2.80~3.80(m, 12H), 3.94(t, 2H), 4.21(t, 2H), 4.30(t, 2H), 4.45(d, 2H), 6.36(t, 1H), 6.50(d, 1H), 6.84~7.02(m, 4H), 7.12~7.40(m, 8H), 7.59(d, 1H), 7.99(s, 1H), 8.19(dd, 1H), 9.50~10.50(br, 1H).

Example 14
4-{3-{4-[(4-Ethylphenyl)methylamino]-3-{3-[4-(2-isopropoxyphenyl)piperazin-1-yl]propoxy}benzoyl}indol-1-yl}butanoic acid dihydrochloride Melting point: 190–194° C. (decomposed); MS(m/z): 717(MH$^+$—2HCl); IR(KBr)cm$^{-1}$: 3308, 1707,1590; NMR(DMSO-d$_6$)δ: 1.16(t, 3H), 1.28(s, 3H), 1.30(s, 3H), 2.01(quint, 2H), 2.18~2.35(m, 4H), 2.57(q, 2H), 2.90~3.80(m, 11H), 4.21(t, 2H), 4.30(t, 2H), 4.45(d, 2H), 4.63(t, 1H), 6.41(t, 1H), 6.49(d, 1H), 6.85~7.02(m, 4H), 7.13~7.40(m, 8H), 7.60(d, 1H), 8.00(s, 1H), 8.20(dd, 1H), 9.80~10.50(br, 1H), 11.50~12.60(br, 1H).

Example 15
4-{3-{3-{3-[4-(2-Methoxyphenyl)piperazin-1-yl]propoxy}-4-[(1-phenyl)ethylamino]benzoyl}indol-1-yl}butanoic acid hydrochloride MS(m/z): 675(MH$^+$—HCl); IR(KBr)cm$^{-1}$: 3372, 1592; NMR(DMSO-d$_6$)δ: 1.55(d, 3H), 1.94~2.26(m, 6H), 2.60~3.10(m, 11H), 3.77(s, 3H), 4.14~4.32(m, 5H), 4.60~4.75(m, 1H), 5.63(d, 1H), 6.43(d, 1H), 6.83~7.00(m, 4H), 7.18~7.47(m, 9H), 7.58(d, 1H), 7.97(s, 1H), 8.19(d, 1H).

Example 16
4-{3-{3-{3-[4-(2-Methoxyphenyl)piperazin-1-yl]propoxy}-4-[(2-methylphenyl)methylamino]benzoyl}indol-1-yl}butanoic acid hydrochloride Melting point: 121–126° C. (decomposed); MS(m/z): 675(MH$^+$—HCl); IR(KBr)cm$^{-1}$: 3325, 1701, 1588; NMR(DMSO-d$_6$)δ: 1.95~2.10(m, 2H), 2.24(t, 2H), 2.25~2.40(m, 2H), 2.37(s, 3H), 3.00~3.70(m, 10H), 3.79(s, 3H), 4.24(t, 2H), 4.31(t, 2H), 4.46(d, 2H), 6.35(t, 1H), 6.42(d, 1H), 6.85~7.40(m, 12H), 7.61(d, 1H), 8.02(s, 1H), 8.21(d, 1H), 10.85(brs, 1H), 12.15(brs, 1H).

Example 17
4-{3-{3-{3-[4-(2-Methoxyphenyl)piperazin-1-yl]propoxy}-4-[(3-methylphenyl)methylamino]benzoyl}indol-1-yl}butanoic acid hydrochloride Melting point: 172–173° C. (decomposed); MS(m/z): 675(MH$^+$—HCl); IR(KBr)cm$^{-1}$: 3347, 1732, 1593; NMR(DMSO-d$_6$)δ: 1.95~2.10(m, 2H), 2.18~2.30(m, 7H), 3.00~3.70(m, 10H), 3.80(s, 3H), 4.22(t, 2H), 4.30(t, 2H), 4.46(d, 2H), 6.43~6.55(m, 2H), 6.80~7.10(m, 5H), 7.13~7.40(m, 7H), 7.60(d, 1H), 8.01(s, 1H), 8.20(d, 1H), 10.80(brs, 1H), 12.15(brs, 1H).

Example 18
4-{3-{4-[(2,4-Dimethylphenyl)methylamino]-3-{3-[4-(2-methoxyphenyl)piperazin-1-yl]propoxy}benzoyl}indol-1-yl}butanoic acid hydrochloride Melting point: 128–130° C. (decomposed); MS(m/z): 639(MH$^+$—HCl); IR(KBr)cm$^{-1}$: 3355, 1721, 1590; NMR(DMSO-d$_6$)δ: 1.95~2.10(m, 2H), 2.15~2.37(m, 10H), 3.00~3.65(m, 10H) 3.79(s, 3H), 4.17~4.27(m, 2H), 4.31(t, 2H), 4.41(d, 2H), 6.24(brs, 1H), 6.41(d, 1H), 6.87~7.14(m, 7H), 7.18~7.41(m, 4H), 7.61(d, 1H), 8.02(s, 1H), 8.21(d, 1H), 10.50~11.00(br, 1H), 11.70~12.20(br, 1H).

Example 19
4-{3-{3-{3-[4-(2-Methoxyphenyl)piperazin-1-yl]propoxy}-4-[(2,4,6-trimethylphenyl)methylamino]benzoyl}indol-1-yl}butanoic acid hydrochloride Melting point: 120–127° C. (decomposed); MS(m/z): 703(MH$^+$—HCl); IR(KBr)cm$^{-1}$: 3450, 1734, 1593, 1518; NMR(CDCl$_3$)δ: 2.15~2.50(m, 15H), 2.90~3.75(m, 10H), 3.86(s, 3H), 4.18(t, 2H), 4.25~4.35(m, 4H), 6.83~7.00(m, 6H), 7.01~7.12(m, 1H), 7.25~7.41(m, 4H), 7.69(dd, 1H), 7.73(s, 1H), 8.43~8.52(m, 1H).

Example 20
Potassium 4-{3-{4-(4-ethylphenyl)methylamino]-3-{3-[4-(2-methoxyphenyl)piperazin-1-yl]propoxy}benzoyl}indol-1-yl}butanoate MS(m/z): 727(MH$^+$); IR(KBr)cm$^{-1}$: 3432, 1591; NMR (CD$_3$OD)δ: 1.21(t,3H), 2.05~2.25(m, 6H), 2.61(q, 2H), 2.75~2.93(m, 6H), 3.00~3.20(m, 4H), 3.85(s, 3H), 4.19~4.38(m, 4H), 4.46(s, 2H), 6.60(d, 1H), 6.83~7.05(m, 4H), 7.12~7.33(m, 6H), 7.35~7.45(m, 2H), 7.55(d, 1H), 7.89(s, 1H), 8.13(d, 1H).

Example 21
4-{3-{4-[(4-Isopropylphenyl)methylamino]-3-{3-[4-(2-methoxyphenyl)piperazin-1-yl]propoxy}benzoyl}indol-1-yl}butanoic acid hydrochloride Melting point: 133–140° C. (decomposed); MS(m/z): 703(MH$^+$—HCl); IR(KBr)cm$^{-1}$: 3301, 1734, 1592; NMR (CDCl$_3$)δ: 1.23(d, 6H), 2.13~2.34(m, 4H) 2.35~2.53(m, 2H), 2.89(sept, 1H), 3.00~3.70(m, 10H), 3.85(s, 3H), 4.17(t, 2H), 4.24(t, 2H), 4.40(s, 2H), 5.20~5.60(br, 1H), 6.65(d, 1H), 6.85~6.95(m, 3H), 7.00~7.11(m, 1H), 7.17~7.41(m, 8H), 7.54(dd, 1H), 7.66(s, 1H), 8.38~8.46(m, 1H).

Example 22
4-{3-{4-[(4-Isobutylphenyl)methylamino]-3-{3-[4-(2-methoxyphenyl)piperazin-1-yl]propoxy}benzoyl}indol-1-yl}butanoic acid hydrochloride Melting point: 133–138° C. (decomposed); MS(m/z): 717(MH$^+$—HCl); IR(KBr)cm$^{-1}$: 3299, 1707, 1592; NMR (DMSO-d$_6$)δ: 0.84(d, 6H), 1.70~1.90(m, 1H), 1.95~2.10(m, 2H), 2.16~2.45(m, 6H), 3.00~3.70(m, 10H), 3.80(s, 3H), 4.15~4.25(m, 2H), 4.30(t, 2H), 4.47(d, 2H), 6.45~6.54(m, 2H), 6.87~7.41(m, 12H), 7.60(d, 1H), 8.02(s, 1H), 8.20(d, 1H), 10.77(brs, 1H), 12.17(brs, 1H).

Example 23
4-{3-{4-[(4-Chlorophenyl)methylamino]-3-{3-[4-(2-methoxyphenyl)piperazin-1-yl]propoxy}benzoyl}indol-1-yl}butanoic acid hydrochloride Melting point: 140–148° C. (decomposed); MS(m/z): 695(MH$^+$—HCl); IR(KBr)cm$^{-1}$: 3301, 1707, 1592; NMR (DMSO-d$_6$)δ: 2.02(quint, 2H), 2.24(t, 2H), 2.32(brs, 2H), 3.00~3.70(m, 10H), 3.80(s, 3H), 4.22(t, 2H), 4.31(t, 2H), 4.50(d, 2H), 6.45(d. 1H), 6.61(t, 1H), 6.88~7.10(m, 4H), 7.18~7.48(m, 8H), 7.60(d, 1H), 8.01(s, 1H), 8.20(dd, 1H).

Example 24
4-{3-{4-[(4-Bromophenyl)methylamino]-3-{3-[4-(2-methoxyphenyl)piperazin-1-yl]propoxy}benzoyl}indol-1-yl}butanoic acid hydrochloride Melting point: 138–144° C. (decomposed); MS(m/z): 739(MH$^+$—HCl); IR(KBr)cm$^{-1}$: 3293, 1707, 1592; NMR (DMSO-d$_6$)δ: 1.94~2.10(m, 2H), 2.16~2.38(m, 4H), 2.90~3.75(m, 10H), 3.80(s, 3H), 4.15~4.25(m, 2H), 4.30(t, 2H), 4.47(d, 2H), 6.44(d, 1H), 6.59(t, 1H), 6.87~7.08(m, 4H), 7.18~7.41(m, 6H), 7.50~7.65(m, 3H), 8.01(s, 1H), 8.20(d, 1H), 10.60~11.00(br, 1H), 11.90~12.30(br, 1H).

Example 25
4-{3-{4-[(4-Methoxyphenyl)methylamino]-3-{3-[4-(2-methoxyphenyl)piperazin-1-yl]propoxy}benzoyl}indol-1-yl}butanoic acid hydrochloride Melting point: 123–130° C. (decomposed); MS(m/z): 691(MH$^+$—HCl); IR(KBr)cm$^{-1}$: 3300, 1725, 1592; NMR (DMSO-d$_6$)δ: 1.95~2.10(m, 2H), 2.17~2.37(m, 4H), 2.90~3.70(m, 10H), 3.72(s, 3H), 3.80(s, 3H), 4.14~4.25(m, 2H), 4.30(t, 2H), 4.42(d, 2H), 6.40~6.54(m, 2H), 6.87~7.08(m, 6H), 7.17~7.40(m, 6H), 7.60(d, 1H), 8.01(s, 1H), 8.20(d, 1H), 10.50~10.90(br, 1H), 11.90~12.40(br, 1H).

Example 26
4-{3-{3-[(4-Ethylphenyl)methylamino]-4-{3-[4-(2-methoxyphenyl)piperazin-1-yl]propoxy}benzoyl}indol-1-yl}butanoic acid hydrochloride Melting point: 120–122° C.; MS(m/z): 689(MH$^+$—HCl); IR(KBr)cm$^{-1}$: 3415, 1719, 1586; NMR(CDCl$_3$)δ: 1.19(t, 3H), 2.03~2.17(m, 2H), 2.19~2.30(m, 2H), 2.30~2.44(m, 2H), 2.59(q, 2H), 3.00~3.50(m, 10H), 3.85(s, 3H), 4.02~4.21(m, 4H), 4.38(s, 2H), 6.75(d, 1H), 6.83~6.95(m, 3H), 7.00~7.19(m, 5H), 7.23~7.40(m, 5H), 7.46(s, 1H), 8.36~8.45(m, 1H).

Chemical structures of compounds obtained in Examples 1 to 26 are shown in Tables 1 to 4.

TABLE 1

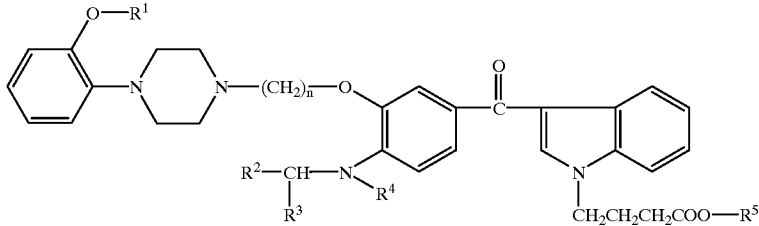

| Example | R$^1$ | n | R$^2$ | R$^3$ | R$^4$ | R$^5$ | Remarks |
|---|---|---|---|---|---|---|---|
| 1 | Me | 3 | H | Et—⟨C$_6$H$_4$⟩— | H | H | hydrochloride |

TABLE 1-continued
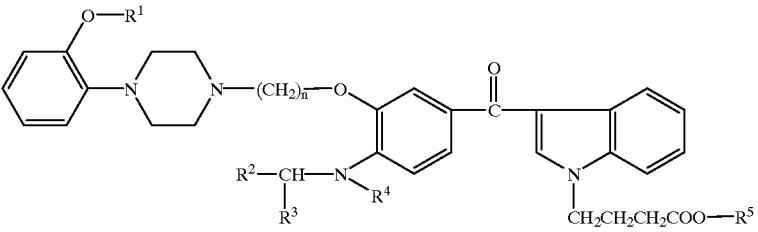
| Example | R¹ | n | R² | R³ | R⁴ | R⁵ | Remarks |
|---|---|---|---|---|---|---|---|
| 2 | Me | 3 | 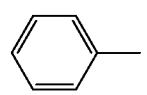 | 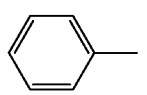 | H | H | hydrochloride |
| 3 | Me | 3 | H | 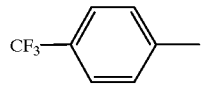 | H | H | hydrochloride |
| 4 | Me | 3 | H | 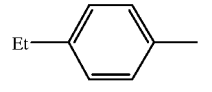 | H | H | |
| 5 | Me | 3 | H | 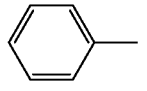 | H | K | |
| 6 | Me | 3 | H | 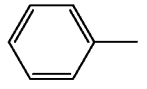 | 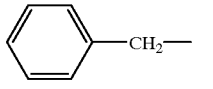 | K | |
| 7 | Me | 3 | H | 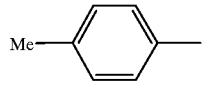 | H | K | |
| 8 | Et | 3 | H | 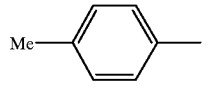 | H | H | |
| 9 | Me | 3 | H | 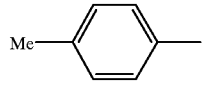 | Me | H | |
| 10 | Et | 3 | H | 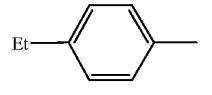 | H | H | |

TABLE 2
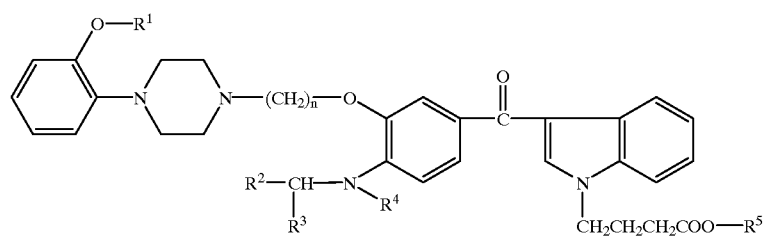
| Example | R¹ | n | R² | R³ | R⁴ | R⁵ | Remarks |
|---------|------|---|-----|----------------|----|----|---------------|
| 11 | Me | 2 | H | 4-Et-phenyl | H | H | hydrochloride |
| 12 | Me | 4 | H | 4-Et-phenyl | H | H | hydrochloride |
| 13 | Pr | 3 | H | 4-Et-phenyl | H | H | dihydrochloride |
| 14 | i-Pr | 3 | H | 4-Et-phenyl | H | H | dihydrochloride |
| 15 | Me | 3 | Me | phenyl | H | H | hydrochloride |
| 16 | Me | 3 | H | 2-Me-phenyl | H | H | hydrochloride |
| 17 | Me | 3 | H | 3-Me-phenyl | H | H | hydrochloride |
| 18 | Me | 3 | H | 2,4-diMe-phenyl | H | H | hydrochloride |
| 19 | Me | 3 | H | 2,3,5-triMe-phenyl | H | H | hydrochloride |
| 20 | Me | 3 | H | 4-Et-phenyl | H | K | |

TABLE 3

[Structure: piperazine compound with O-R¹, (CH₂)ₙ-O, R²-CH(R³)-N(R⁴), and CH₂CH₂CH₂COO-R⁵ groups on indole]

| Example | R¹ | n | R² | R³ | R⁴ | R⁵ | Remarks |
|---------|----|----|----|----|----|----|---------|
| 21 | Me | 3 | H | 4-(Me₂CH)-C₆H₄- | H | H | hydrochloride |
| 22 | Me | 3 | H | 4-(Me₂CHCH₂)-C₆H₄- | H | H | hydrochloride |
| 23 | Me | 3 | H | 4-Cl-C₆H₄- | H | H | hydrochloride |
| 24 | Me | 3 | H | 4-Br-C₆H₄- | H | H | hydrochloride |
| 25 | Me | 3 | H | 4-MeO-C₆H₄- | H | H | hydrochloride |

TABLE 4

[Structure: same general formula as Table 3]

| Example | R¹ | n | R² | R³ | R⁴ | R⁵ | Remarks |
|---------|----|----|----|----|----|----|---------|
| 26 | Me | 3 | H | 4-Et-C₆H₄- | H | H | hydrochloride |

Action

<α₁-Adrenergic Receptor Blocking Action

Rabbits were sacrificed by exsanguination, and in each rabbit the urethra and prostate were isolated from the lower urinary tract system. Transverse smooth muscle strips were prepared. Each strip was suspended in a 37° C. Krebs-solution-containing organ bath which had been bubbled with 95% $O_2$ and 5% $CO_2$. Isometric contraction under a resting tension of 1 g was recorded with an isometric transducer (TB-651T, Nihon Koden) on a thermal pen-type recorder (RECTI HORIZ 8K, Nihon Denki San'ei).

The strip was allowed to stand for equilibration for 60 minutes, and contractions were elicited by a certain concentration of phenylephrine ($10^{-5}$ M). The organ bath was washed with a nutrient liquid. Thereafter, the above procedure was repeated at 60-minute intervals until constant contraction responses were obtained. Subsequently, dose-response curves were obtained by administration of phenylephrine in an accumulative manner ($10^{-7}$ to $3\times10^{-4}$ M). After the strips were washed and then rested for 60 minutes, the strips were treated with a test drug solution (i.e., DMSO solution containing the test drug; $10^{-7}$ to $10^{-5}$ M) for 30 minutes, to thereby obtain dose-response curves for phenylephrine.

The composition of the nutrient solution was as follows.

NaCl 118.4 mM, KCl 4.7 mM, $MgCl_2$ 1.2 mM, $CaCl_2$ 2.5 mM, $NaHCO_3$ 25.0 mM, glucose 1.1 mM, $KH_2PO_4$ 1.2 mM.

In all cases, $10^{-5}$ M propranolol (β-adrenaline antagonist) was administered 10 minutes before administration of the drug.

The efficacy of each test drug in terms of $α_1$-adrenergic receptor blocking action was assessed from calculation of $pA_2$ (inverse of logarithm of the mole concentration of antagonist which requires, in the presence of an antagonist, twice the concentration of an agonist that provides an effect equal to that obtained in the absence of an antagonist). The results are shown in Table 5.

TABLE 5

$α_1$-Adrenergic Receptor Blocking Action

| Example No. | Urethra ($pA_2$) | Prostate ($pA_2$) |
| --- | --- | --- |
| 1 | 6.52 | 6.65 |
| 5 | 6.76 | 7.27 |
| 7 | 6.50 | 7.02 |

Test Example 2

<Testosterone 5α-Reductase Inhibitory Action>

Male Wistar rats (age: 9–10 weeks old) were anesthetized with ether. The abdomen of each rat was median-cut to thereby remove the prostate. The isolated prostates were weighed and homogenized in 3 tissue volumes of 50 mM Tris-HCl buffer (pH 7.2) containing 0.25 M sucrose. The homogenates were filtered with gauze and centrifuged at 3,000 rpm for 10 minutes. The pellets were resuspended in a buffer as described above and the resultant suspension was used as a nuclear fraction.

The nuclear fraction of the prostates (0.1 ml), 5 mM NADPH (0.1 ml), and a test drug solution (DMSO solution containing the test drug; 0.01 ml) were added to 50 mM Tris-HCl buffer (pH 7.0; 0.78 ml). Reaction was initiated by addition of 150 μM [$4$-$^{14}$C]-testosterone (0.01 ml) to the resultant solution, and the reaction mixture was incubated for 60 minutes at 37° C. After incubation, reaction was stopped by addition of ethyl acetate (4 ml), and simultaneously, the reaction mixture was subjected to extraction. The extract (3 ml) was brought to dryness through evaporation with nitrogen gas. Ethyl acetate (40 μl) was added thereto, and a 10 μl portion was applied to a silica gel thin layer plate for development with a solvent mixture of ethyl acetate and cyclohexane (1:1). After development, the plate was subjected to autoradiography, and spots attributed to testosterone, dihydrotestosterone, and other metabolites were collected by scraping. Radioactivity of the spots was counted in a liquid scintillation counter. From the total radioactivity and the radioactivity of 5α-metabolites, reaction ratio was obtained. $IC_{50}$ of the compound, which represents the inhibitory activity of the test compound, was calculated from the reaction ratio of the control solvent and the reaction ratio obtained when the compound was added. The results are shown in Table 6.

TABLE 6

Testosterone 5 α-Reductase Inhibitory Action

| Example No. | $IC_{50}$ (nM) |
| --- | --- |
| 1 | 0.70 |
| 7 | 0.86 |
| 8 | 1.0 |
| 10 | 0.47 |

<Toxicity Test>

Groups of ICR mice (Charles River, age: 4–5 weeks old), each group consisting of 10 mice, were used. A compound of each Example was suspended in 10% gum arabic. The suspension was intraperitoneally administered to each mouse at a dose of 100 mg/kg. The mice were observed over 7 days. No casualties occured at this dosage.

Preparation Example 1

The compound (20 g) of Example 1, lactose (315 g), corn starch (125 g), and crystalline cellulose (25 g) were mixed uniformity. An 7.5% aqueous hydroxypropylcellulose solution (200 ml) was added thereto. The resultant mixture was granulated with an extruder equipped with a screen having a mesh of 0.5 mm diameter. The thus-prepared granules were immediately rounded with a marumerizer and then dried, providing a granular agent.

Preparation Example 2

By use of a fluidized granulator, granules prepared in Preparation Example 1 were coated with a film coating liquid (1.9 kg) having the following composition, thereby obtaining an enteric granular agent.

Composition of coating liquid: hydroxypropylmethylcellulose phthalate (5.0%), stearic acid (0.25%), methylene chloride (50.0%), and ethanol (44.75%).

Preparation Example 3

The compound (20 g) of Example 17, lactose (100 g), corn starch (36 g), crystalline cellulose (30 g), calcium carboxymethylcellulose (10 g), and magnesium stearate (4 g) were mixed uniformly. The resultant mixture was formed into tablets, 200 mg each, by use of a single-punch tableting machine having a pestle of 7.5 mm in diameter.

Preparation Example 4

Tablets prepared in Preparation Example 3 were spray-coated with a coating liquid having the following composition, thereby providing enteric film-coated tablets, each coated with 10 mg of coating.

Composition of coating liquid: hydroxypropylmethylcellulose phthalate (8.0%), maibaset (0.4%), methylene chloride (50.0%), bleached beeswax (0.1%), and isopropanol (41.5%)

Preparation Example 5

The compound (200 g) of Example 17, polysorbate 80 (20 g), and medium chain fatty acid triglyceride (1780 g) were mixed and dissolved completely. Subsequently, the resultant solution was formed into a soft capsulated agent, each capsule containing 200 mg of the solution, by a rotary method using a coating liquid for soft capsules, which is composed of gelatin (100 parts), thick glycerin (30 parts), ethyl paraben (0.4 parts), and propyl paraben (0.2 parts).

Preparation Example 6

Compound of Example 22 100 mg
Sodium acetate 2 mg
Acetic acid (to adjust to pH 5.8)
  Suitable amount
Distilled water Balance
Total 10 ml/vial The above ingredients were processed by a routine method to obtain an injection agent.

Industrial Applicability

The compound (I) of the present invention has both strong $\alpha_1$-adrenergic receptor blocking action and strong testosterone $5\alpha$-reductase inhibitory action, and thus is useful as a remedy and/or a preventive for disorders; e.g., prostatic hypertrophy or accompanying urination disorder, male pattern alopecia, and acne (acne, pimples, etc.).

What is claimed is:

1. A 3-benzoylindole derivative of formula (I) or a pharmaceutically acceptable salt thereof:

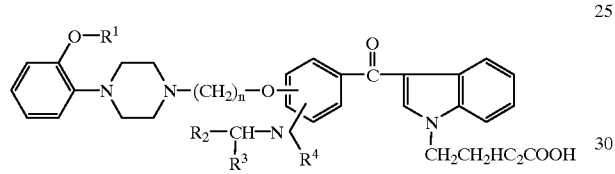

(I)

wherein $R^1$ represents a lower alkyl group, n is an integer from 1 to 5; each of $R^2$ and $R^3$ are the same or different and each independently represents a hydrogen atom, a lower alkyl group, or a phenyl group which may have one or more substituents selected from the group consisting of a lower alkyl group, a halo-substituted lower alkyl group, a lower alkoxy group, and a halogen atom; and $R^4$ represents a hydrogen atom, a lower alkyl group, or a benzyl group.

2. A 3-benzoylindole derivative or a salt thereof according to claim 1, wherein $R^2$ is a hydrogen atom, a lower alkyl group, or a phenyl group, and $R^3$ is a phenyl group which may have one or more substituents selected from among lower alkyl group, a halo-substituted lower alkyl group, a lower alkoxy group, and a halogen atom.

3. A pharmaceutical composition comprising a 3-benzoylindole derivative of formula (I) or a salt thereof as defined in claims 1 or 2, and a pharmaceutically acceptable carrier.

4. A method for treating prostatic hypertrophy, urination disorders associated with prostatic hypertrophy, male pattern alopecia, or acne in a subject, which comprises administering to said subject an effective amount of a 3-benzoylindole derivative or a salt thereof as defined in claims 1 or 2.

* * * * *